US009221271B2

(12) United States Patent
Eller et al.

(10) Patent No.: US 9,221,271 B2
(45) Date of Patent: *Dec. 29, 2015

(54) SYSTEMS AND METHODS FOR PHARMACY MESSAGING

(71) Applicant: Express Scripts, Inc., St. Louis, MO (US)

(72) Inventors: Charles E. Eller, Lake Saint Louis, MO (US); Jacob J. Reinhardt, Wentzville, MO (US); Katherine H. Sundararaman, St. Louis, MO (US)

(73) Assignee: Express Scripts, Inc., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/313,042

(22) Filed: Jun. 24, 2014

(65) Prior Publication Data

US 2014/0300681 A1 Oct. 9, 2014

Related U.S. Application Data

(63) Continuation of application No. 13/788,383, filed on Mar. 7, 2013, now Pat. No. 8,786,650.

(60) Provisional application No. 61/607,717, filed on Mar. 7, 2012.

(51) Int. Cl.
| | |
|---|---|
| *B41J 2/435* | (2006.01) |
| *G06Q 10/00* | (2012.01) |
| *G06Q 50/00* | (2012.01) |
| *B41J 2/455* | (2006.01) |
| *B41J 3/407* | (2006.01) |
| *B23K 26/06* | (2014.01) |

(52) U.S. Cl.
CPC .............. *B41J 2/455* (2013.01); *B23K 26/0608* (2013.01); *B41J 2/435* (2013.01); *B41J 3/4073* (2013.01)

(58) Field of Classification Search
USPC ........................... 347/224, 225, 110; 705/2–4
See application file for complete search history.

(56) References Cited

U.S. PATENT DOCUMENTS

| | | | |
|---|---|---|---|
| 5,612,869 A | | 3/1997 | Letzt et al. |
| 5,658,474 A | * | 8/1997 | Geerke .................... 219/121.71 |
| 5,824,715 A | * | 10/1998 | Hayashihara et al. .......... 522/14 |
| 6,105,806 A | * | 8/2000 | Stasiuk ......................... 220/269 |
| 6,240,394 B1 | | 5/2001 | Uecker et al. |
| 6,947,900 B2 | | 9/2005 | Giordano, III et al. |

(Continued)

FOREIGN PATENT DOCUMENTS

| | | | |
|---|---|---|---|
| FR | 2848499 A1 | 6/2004 | |
| WO | WO 2007104854 A3 * | 11/2007 | ............. B23K 26/12 |

*Primary Examiner* — Hai C Pham
(74) *Attorney, Agent, or Firm* — Husch Blackwell LLP

(57) ABSTRACT

Systems and methods for pharmacy messaging are described. A system includes a laser module and a control module. The laser module includes a marking chamber with a plurality of laser heads therein. A first and second entry gate are adjacent the marking chamber. The first entry gate is configured to open when the second entry gate is closed. A first and second exit gate are adjacent the marking chamber at a side different from the first entry and second entry gate. The first exit gate is configured to open when the second exit gate is closed. A transporter moves the objects being marked into and out of the marking chamber through the various gates. The control module is communicatively coupled to the laser module and adapted to control the laser module. Additional methods and systems are disclosed.

24 Claims, 12 Drawing Sheets

(56) References Cited

U.S. PATENT DOCUMENTS

| | | |
|---|---|---|
| 6,973,371 B1 | 12/2005 | Benouali |
| 6,985,869 B1 | 1/2006 | Stoll et al. |
| 7,158,030 B2 | 1/2007 | Chung |
| 7,329,830 B2 | 2/2008 | Baudron et al. |
| 7,558,380 B2 | 7/2009 | DiVenuta et al. |
| 7,848,934 B2 | 12/2010 | Kobylevsky et al. |
| 7,957,984 B1 | 6/2011 | Vallone |
| 8,786,650 B1 * | 7/2014 | Eller et al. .................... 347/224 |
| 8,803,028 B1 * | 8/2014 | Daily ....................... 219/121.68 |
| 2002/0035484 A1 | 3/2002 | McCormick |
| 2002/0052762 A1 | 5/2002 | Kobylevsky et al. |
| 2002/0138302 A1 | 9/2002 | Bodnick |
| 2003/0024089 A1 * | 2/2003 | Dziekonski ........................ 27/1 |
| 2004/0010418 A1 | 1/2004 | Buonocore et al. |
| 2004/0059602 A1 | 3/2004 | Ball et al. |
| 2004/0059607 A1 | 3/2004 | Ball et al. |
| 2004/0181428 A1 | 9/2004 | Fotsch et al. |
| 2004/0181430 A1 | 9/2004 | Fotsch et al. |
| 2004/0220829 A1 | 11/2004 | Baharav et al. |
| 2005/0060200 A1 | 3/2005 | Kobylevsky et al. |
| 2005/0114182 A1 | 5/2005 | Randolph et al. |
| 2005/0144038 A1 | 6/2005 | Tamblyn et al. |
| 2005/0267356 A1 * | 12/2005 | Ramasubramanian et al. ............................. 600/411 |
| 2006/0122866 A1 | 6/2006 | Hadl et al. |
| 2007/0009090 A1 * | 1/2007 | Stichelbaut et al. ............ 378/69 |
| 2007/0168228 A1 | 7/2007 | Lawless |
| 2007/0174092 A1 | 7/2007 | Lara et al. |
| 2008/0091475 A1 | 4/2008 | Sottile |
| 2008/0126130 A1 | 5/2008 | Miller et al. |
| 2008/0183500 A1 | 7/2008 | Banigan |
| 2008/0208628 A1 | 8/2008 | Kobylevsky et al. |
| 2008/0312965 A1 | 12/2008 | Meshginpoosh |
| 2008/0312966 A1 | 12/2008 | Meshginpoosh |
| 2009/0037221 A1 | 2/2009 | Litherland et al. |
| 2009/0043608 A1 | 2/2009 | Nadas et al. |
| 2009/0210255 A1 | 8/2009 | Leon |
| 2009/0281835 A1 | 11/2009 | Patwardhan et al. |
| 2009/0287502 A1 | 11/2009 | Roberts et al. |
| 2010/0082367 A1 | 4/2010 | Hains et al. |
| 2010/0314282 A1 | 12/2010 | Bowers |
| 2011/0082705 A1 | 4/2011 | Kobylevsky et al. |
| 2013/0173277 A1 | 7/2013 | Eller et al. |

* cited by examiner

SYSTEMS AND METHODS FOR PHARMACY MESSAGING

CROSS-REFERENCE TO A RELATED APPLICATION

This application claims priority to and is a continuation of U.S. patent application Ser. No. 13/788,383 filed Mar. 7, 2013, said application claiming priority to U.S. Provisional Patent Application Ser. No. 61/607,717, filed on Mar. 7, 2012, entitled "Systems and Methods for Pharmacy Messaging," the entire disclosures of which are incorporated herein by reference.

FIELD

The field relates to marking systems, and more particularly to a system for marking caps of members with messages.

BACKGROUND

Prescription medications, if taken as prescribed, may have a positive impact to a person's health. Nevertheless, patients of a pharmacy often do not take their prescription drugs properly. Indeed, consistently taking medications on schedule may prove difficult to the patient. Whether it is from forgetfulness, inconvenience, or discomfort, doses are often missed. In addition, patients often do not timely renew or refill their prescription, or may even quit taking the prescribed medication altogether. Some patients may intend to continue taking the prescribed medication but wait too long to reorder additional prescription drugs. In other words, patients may miss doses because they are waiting for the renewal or refill of a prescription to be filled. Additionally, for a renewal, the pharmacy generally requires a new written prescription from the patient's doctor approving the continuation of therapy. In this case, it is likely that the doctor would request an office visit before writing the prescription. Scheduling conflicts and overall delays due to the required visit can result in prolonged nonadherence to the drug regimen. The patient's health and well-being may be adversely affected.

In addition to varying degrees of nonadherence to a drug regimen, patients may not be aware of certain opportunities. The opportunity may be as simple as a lower cost, alternative, chemically-equivalent drug is available, or the patient may have become eligible for a promotional savings. In yet another example, a new convenience feature may have been added to the patients' pharmacy benefit plan but requires action to reap the benefits.

DETAILED DESCRIPTION

Figure 1:
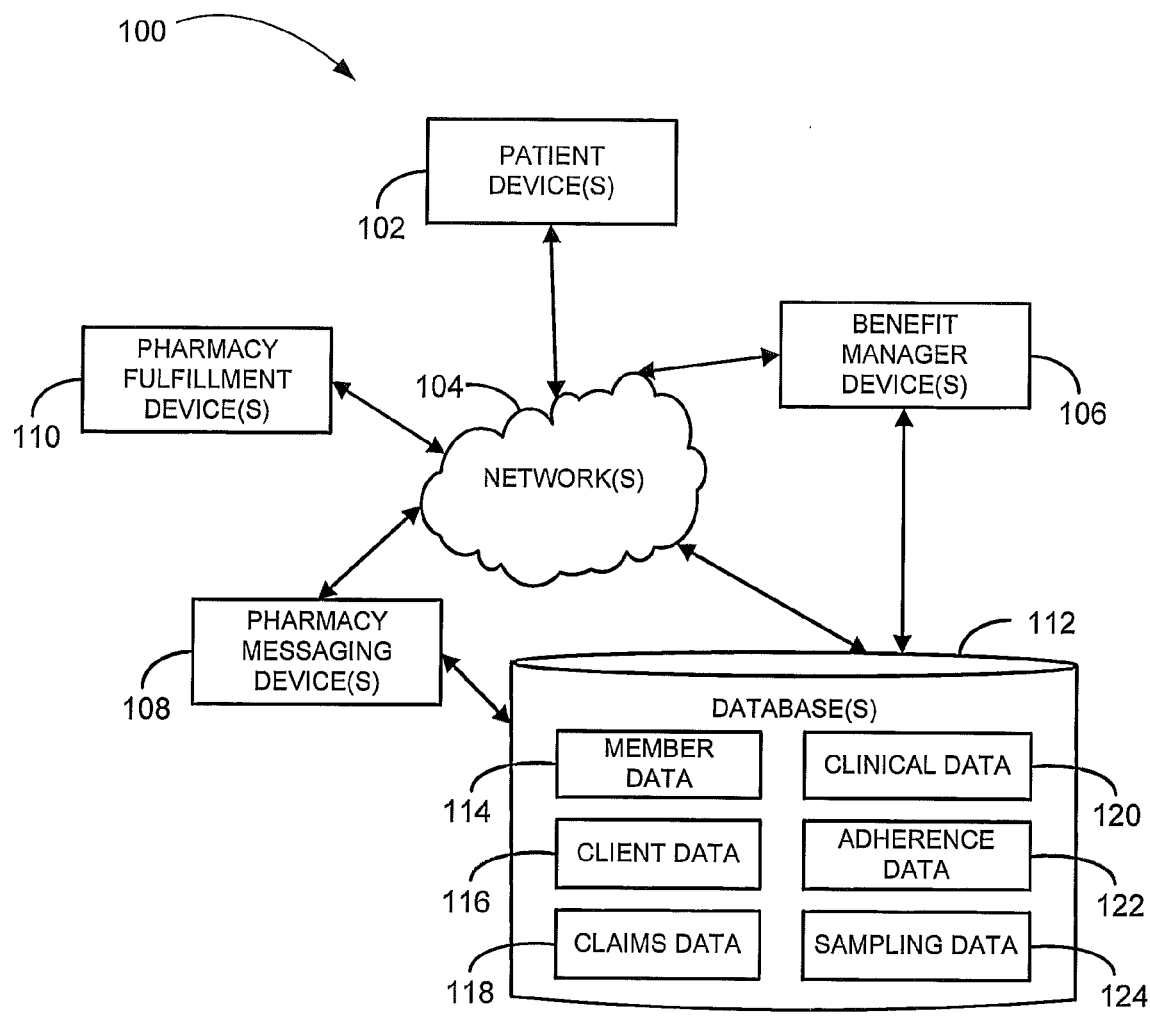
FIG. 1 is a block diagram of an example system according to an example embodiment.

Example systems and methods for pharmacy messaging are described. In the following description, for purposes of explanation, numerous specific details are set forth in order to provide a thorough understanding of example embodiments. It will be evident, however, to one of ordinary skill in the art that embodiments of the invention may be practiced without these specific details.

In general, a client engages a pharmacy benefit manager (PBM) to offer a drug benefit program. Examples of clients include governmental organizations (e.g., Federal government agencies, the Department of Defense, the Centers for Medicare and Medicaid Services and state government agencies), middle market companies, large national employers, health insurance companies that have carved out the drug benefit, and the like. A person who is a participant or member of a drug benefit program offered by the client may obtain prescription drugs according to pricing, pharmacy selection, rebates, discounts and the like provided by the terms of the drug benefit program.

The client's offered drug benefit program may be a stand-alone drug benefit operated by the PBM, or as part of a health care benefit operated by a health insurance company where the PBM services are offered directly by the health insurance company or offered indirectly by the PBM on behalf of the health insurance company.

Some of the operations of the PBM may include the following. A member or a person acting on behalf of the member attempts to obtain a prescription drug at a retail pharmacy location of a pharmacy where the member can obtain drugs in a physical store from a pharmacist or pharmacist technician. The pharmacy can be associated with a single retail pharmacy location, or can be a pharmacy chain that includes multiple retail pharmacy locations. The pharmacy then submits a claim to the PBM for the prescription drug. The PBM performs certain adjudication operations including verifying the eligibility of the member, reviewing the formulary to determine appropriate co-pay, coinsurance, and deductible for the prescription drug, and performing a drug utilization review (DUR) on the member. The PBM then provides a response to the pharmacy following performance of the aforementioned operations. The aforementioned adjudication operations generally occur before the co-pay is received and the prescription drug dispensed. However, the operations may occur simultaneously, substantially simultaneously, or in a different order. In addition, more or less adjudication functions may be performed as part of the adjudication process.

As part of the adjudication, the client (or typically the PBM on behalf of the client) ultimately reimburses the pharmacy for filling the prescription drug when the prescription drug was successfully adjudicated. The amount of reimbursement paid to the pharmacy by the client and/or PBM may be based at least in part on the type of pharmacy network in which the pharmacy is included. Other factors may be used to determine the reimbursement amount in addition to the type of pharmacy network. In an embodiment in which the PBM reimburses the pharmacy on behalf of the client, the PBM may subsequently bill the client for the amount of the reimbursement, and typically also for the services of the PBM in adjudicating the claim and otherwise managing the drug benefit program. The amount that the client is billed by the PBM may be based at least in part on the reimbursement paid to the pharmacy, the type of pharmacy network in which the pharmacy is included. Other factors may be used to determine the billed amount.

The PBM may offer mail order drugs as part of its services, or a third party may offer mail order drugs to members of the PBM. The PBM may adjudicate the pharmacy claim for the mail order prescription drugs in the same or a similar manner to the process described above.

As part of the services that the PBM offers to the client, the services offered through a mail order pharmacy and/or retail pharmacy, or otherwise to the member, the PBM may seek to reduce the cost to the client for the prescription drugs taken by its members and/or to improve the adherence of the members of a prescription drug regimen. The PBM, the mail order pharmacy, and/or the retail pharmacy may mark caps of prescription drugs with messaging including text, images, or the like to remind the member to take a prescription drug, timely refill the prescription drug, or otherwise take one, or more than one, actions.

FIG. 1 is a block diagram of an example system 100, according to an example embodiment. The system 100 is an example embodiment in which pharmacy messaging may be performed. The system 100 includes a patient device 102 in communication with a benefit manager device 106 over a network 104. The system may also include a pharmacy messaging device 108 and a pharmacy fulfillment device 110.

The patient device 102 is used by a device operator. The device operator may be a member of a drug benefit program. However, the device operator may be another person operating the patient device 102 on behalf of the member. Examples of such people include parents, guardians and caregivers. Accordingly, while some illustrative embodiments may be described herein in which the device operator may be the member, the device operator may be an individual other than the member. In some embodiments, the device operator may be a patient of a pharmacy who is not a member of PBM. While the member is generally described herein as being the device operator, generally any of the aforementioned persons may be substituted for the member.

In some embodiments, the member may utilize the patient device 102 to communicate with the benefit manager (e.g., through the benefit manager device 106) or a pharmacy (e.g., through the pharmacy messaging device 108 and/or the pharmacy fulfillment device 110). Examples of the patient device 102 include a set-top box (STB), a receiver card, a mobile telephone, a personal digital assistant (PDA), a display device, a portable gaming unit, a smart prescription drug cap or capper, and a computing system; however other devices may also be used. For example, the patient device 102 may include a mobile electronic device, such an IPHONE or IPAD device by Apple, Inc., mobile electronic devices powered by ANDROID by Google, Inc., and a BLACKBERRY device by Research In Motion Limited. The patient device 102 may also include other computing devices, such as desktop computing devices, notebook computing devices, netbook computing devices, gaming devices, and the like. Other types of electronic devices may also be used.

In some embodiments, the member may use, in addition to or instead of the patient device 102, a telephone, a fax machine, or postal mail to communicate with various devices in the network 104 and/or organizations associated with these devices.

The network 104 by which the patient device 102 communicates with the benefit manager device 106, the pharmacy messaging device 108, and/or the pharmacy fulfillment device 110 may include, by way of example, Mobile Communications (GSM) network, a code division multiple access (CDMA) network, 3rd Generation Partnership Project (3GPP), an Internet Protocol (IP) network, a Wireless Application Protocol (WAP) network, a WiFi network, or an IEEE 802.11 standards network, as well as various combinations thereof. Network 104 may also include optical communications. Other conventional and/or later developed wired and wireless networks may also be used. In some embodiments, the network 104 may include a prescribing network such as the electronic prescribing network operated by Surescripts of Arlington, Va.

The benefit manager device 106 is a device operated by an entity at least partially responsible for the management of a drug benefit program. While the entity operating the benefit manager device 106 is typically a PBM, other entities may operate the benefit manager device 106 either on behalf of themselves, the PBM, or another entity. In some embodiments, the benefit manager that provides the drug benefit may also provide one or more than one additional benefits including a health benefit, a dental benefit, a vision benefit, a wellness benefit, a radiology benefit, a pet care benefit, an insurance benefit, a long term care benefit, a nursing home benefit, and the like.

Some of the operations of the PBM that operates the benefit manager device 106 may include the following. A member (or a person on behalf of the member) attempts to obtain a prescription drug at a retail pharmacy location where the member can obtain drugs in a physical store from a pharmacist or pharmacist technician, or in some instances through mail order drug delivery from a mail order pharmacy location.

The member may have a co-pay for the prescription drug that reflects an amount of money that the member is responsible to pay the pharmacy for the prescription drug. The money paid by the member to the pharmacy may come from the personal funds of the member, a health savings account (HSA) of the member or the member's family, a health reimbursement arrangement (HRA) of the member or the member's family, a flexible spending accounts (FSA) of the member or the member's family, or the like. An employer of the member may directly or indirectly fund or reimburse the member or an account of the member for the co-pay.

The amount of the co-pay paid by the member may vary by the benefit plan of the client with the PBM. The member's co-pay may be based on be a flat co-pay (e.g., $10), co-insurance (e.g., 10%), and/or a deductible (e.g., for first $500 of annual prescription drug spend) for certain prescription drugs, certain types of prescription drugs, and/or all prescription drugs.

In certain instances, the member may not pay the co-pay or may only pay for a portion of a co-pay for a prescription drug. For example, if the usual and customary cost for a generic version of a prescription drug is $4, and the member's flat co-pay is $20 for the prescription drug, the member may only pay $4 to receive the prescription drug. In another example involving a worker's compensation claim, no co-pay may be due by the member for the prescription drug.

In conjunction with receiving the co-pay (if any) from the member and dispensing the prescription drug to the member, the pharmacy submits a claim to the PBM for the prescription drug. The PBM may perform certain adjudication operations including verifying the eligibility of the member, reviewing the formulary to determine appropriate co-pay, coinsurance, and deductible for the prescription drug, and performing a DUR on the member. The PBM then provides a response to the pharmacy following performance of the aforementioned operations. As part of the adjudication, the client (or the PBM on behalf of the client) ultimately reimburses the pharmacy for filling the prescription drug when the prescription drug was successfully adjudicated. The aforementioned adjudication operations generally occur before the co-pay is received and the prescription drug dispensed. However, the operations may occur simultaneously, substantially simultaneously, or in a different order. In addition, more or less adjudication operations may be performed as part of the adjudication process.

The PBM, a pharmacy, or another entity may offer member (or patient) messaging. The messaging may be offered as a service by the offering entity, may be requested by the member, or may otherwise be provided. The pharmacy messaging device 108 may be in communication with the one, or more than one, of the other devices 102, 106, 110 of the system 100 to enable messaging.

In some embodiments, the pharmacy messaging device 108 selects from available messages to generate messages for the member. The pharmacy messaging device 108 may, in some embodiments, evaluate predicted messages from a predictive model with a member's selected preferences. If the member's selected preferences contradict the predicted message, the pharmacy messaging device 108 may determine whether to generate the message for sending to the member based on priority, rules based, or adaptive systems.

The pharmacy fulfillment device 110 may include hardware and/or software of a mail order pharmacy and/or or a retail pharmacy to enable the pharmacy to fulfill prescription drug orders. The pharmacy fulfillment device 110 may be operated in an automated manner, as directed by an operator (e.g., a pharmacist or pharmacist technician), or otherwise. Examples of pharmacy operations that may be performed by pharmacy fulfillment device 110 include filling a prescription after removing pharmaceuticals from inventory, labeling a container with prescription information, filling a container with the pharmaceutical, verifying the type and quantity of the pharmaceutical in the container with that which is printed on the label, and the like. Unit of use products (pre-packaged items) may be used in which case the pharmacy operations would not include filling a container.

In some embodiments, the pharmacy fulfillment device 110 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. In some embodiments, the pharmacy fulfillment device 110 may be utilized by the pharmacy to submit the claim to the PBM for adjudication. Additionally, in some embodiments, the pharmacy fulfillment device 110 may enable information exchange between the pharmacy and the PBM, for example, to allow the sharing of member information such as drug history, and the like, that may allow the pharmacy to better service a member (e.g., by providing more informed therapy consultation and drug interaction information, etc.).

The pharmacy fulfillment device 110, in some embodiments, enables filling operations in a mail order pharmacy or a retail pharmacy. The pharmacy fulfillment device 110 provides capping of prescription containers with various colored caps or rings. The caps and rings may be painted a desired color or may be pulled from inventory. The pharmacy fulfillment device 110 may include machines to coordinate painting or delivery from inventory.

The pharmacy fulfillment device 110 may have the capability to apply messages to various surfaces. The pharmacy fulfillment device 110 may have printing capability to print messages on labels or on paper inserts (e.g., a note in the bottle), the cap, or any article included in or with the prescription packaging. The pharmacy fulfillment device 110 may also utilize lasers for applying an image, adherence score, adherence grade, or a text message to the cap of a prescription container. The cap may be treated with a suitable material to enable the laser marking.

The benefit manager device 106 and/or the pharmacy messaging device 108 may be in communication directly (e.g., through local storage) and/or through the network 104 (e.g., in a cloud configuration or software-as-a-service) with a device that stores a database 112. The database 112 may be deployed on the benefit manager device 106, the pharmacy messaging device 108, both the patient device 102 and the pharmacy messaging device 108, partially on the benefit manager device 106 and partially on the pharmacy messaging device 108, on a separate device, or may otherwise be deployed. The database 112 may store member data 114, client data 116, claims data 118, clinical data 120, adherence data 122, and/or sampling data 124.

The member data 114 includes information regarding the members associated with the benefit manager. Examples of the member data 114 include name, address, telephone number, e-mail address, prescription drug history, and the like. The member data 114 may include a member identifier that identifies the member as a client of the pharmacy and/or identifies the member as a member of a PBM. The member data 114 may include data collected by the patient device 102. The member data 116 may also include member preferences.

The client data 116 includes information regarding the clients of the benefit manager. Examples of the client data 116 include company name, company address, contact name, contact telephone number, contact e-mail address, and the like. The client data 116 may also include client preferences on a client level and/or on a member level.

The claims data 118 may include medical, dental, vision, and/or prescription drug claims made by or on behalf of the member. In some embodiments, the claims data 118 may include prescription drug claims that have been adjudicated for each member of a drug benefit program (e.g., prescribed drugs, prescription history, pharmacy usage, co-pay information, and the like).

The claims data 118 generally includes information regarding prescription drug claims or pharmacy claims adjudicated by the PBM under a drug benefit program provided by the PBM for one, or more than one, clients. In general, the claims data 118 includes an identification of the client that sponsors the drug benefit program under which the claim is made, and/or the member that purchased the prescription drug giving rise to the claim, the prescription drug that was filled by the pharmacy, and the price of the prescription drug provided under the drug benefit program. Additional information may be included in the various claims of the claims data 118.

The clinical data 120 may include clinical records regarding member diagnosis and/or therapy. The clinical records may be obtained from hospitals, medical insurance companies, drug trials, medical laboratories and/or the member via online questionnaires, for example.

The adherence data 122 may include medical, dental, vision, and/or prescription insurance claims made by the member. The adherence data 122 may be gathered from member questionnaires or adherence monitoring devices such as a smart cap or capper. The adherence data 122 may include data gathered through past frequency of prescription drug orders and calculated remaining supply, if any, of the prescription drug ordered each time.

The sampling data 124 may include demographic data of the member. The sampling data 124 includes statistical characteristics of members in certain groups. The members may be grouped by type of drug taken, level of adherence, or insurance carrier, for example. Statistical characteristics may include employment status, marital status, location, gender, age, disabilities, and mobility. The sampling data 124 may be obtained from government agencies, hospitals, medical insurance companies, drug trials, medical laboratories, and/or the member via online questionnaires, for example. The sampling data 124 may also include information from pilot programs conducted by the pharmacy or a third party. The sampling data 124 may also be used to establish pilot programs by identifying sub-sets of members for test messages.

While the system 100 in FIG. 1 is shown to include single devices 102, 106, 108, 110 multiple devices may be used. The devices 102, 106, 108, 110 may be the same type of device or may be different device types. When multiple devices are present, the multiple devices may be of the same device type or may be a different device type. Moreover, system 100 shows a single network 104, however, multiple networks can be used. The multiple networks may communicate in series with each other to link the devices 102, 106, 108, 110 or in parallel to link the devices 102, 106, 108, 110.

Figure 2:
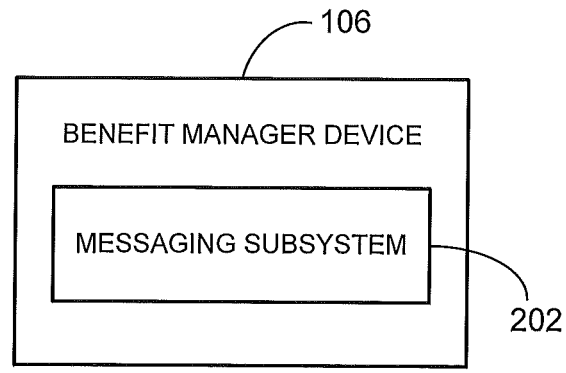
FIG. 2 is a block diagram of an example benefit manager device that may be deployed within the system of FIG. 1, according to an example embodiment.

FIG. 2 illustrates the benefit manager device 106, according to an example embodiment. The benefit manager device 106 may include a messaging subsystem 202. The messaging subsystem 202 may enable generation of a message to a member. The benefit manager device 106 may be deployed in the system 100, or may otherwise be used.

Figure 3:
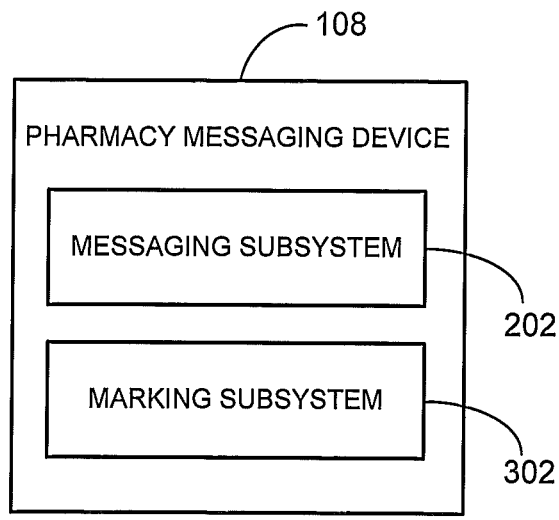
FIG. 3 is a block diagram of an example pharmacy messaging device that may be deployed within the system of FIG. 1, according to an example embodiment.

FIG. 3 illustrates the pharmacy messaging device 108, according to an example embodiment. The pharmacy messaging device 108 may include the messaging subsystem 202 and/or the marking subsystem 302. The messaging subsystem 202 may enable generation of a message to a member. The marking subsystem 302 may enable marking of a prescription (e.g., a cap of the prescription) based on generation of the message to the member. The pharmacy messaging device 108 may be deployed in the system 100, or may otherwise be used.

Figure 4:
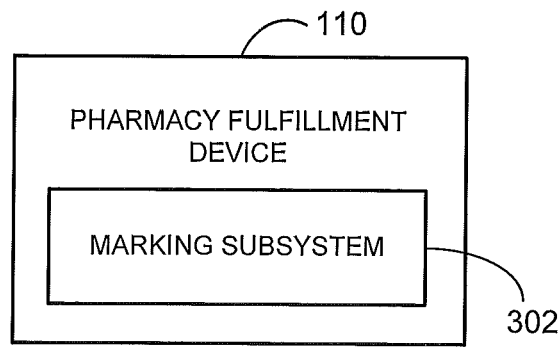
FIG. 4 is a block diagram of an example pharmacy fulfillment device that may be deployed within the system of FIG. 1, according to an example embodiment.

FIG. 4 illustrates the pharmacy fulfillment device 110, according to an example embodiment. The pharmacy fulfillment device 110 may include the marking subsystem 302. The marking subsystem 302 may enable marking of a prescription based on generation of the message to the member. The pharmacy fulfillment device 110 may be deployed in the system 100, or may otherwise be used.

Figure 5:
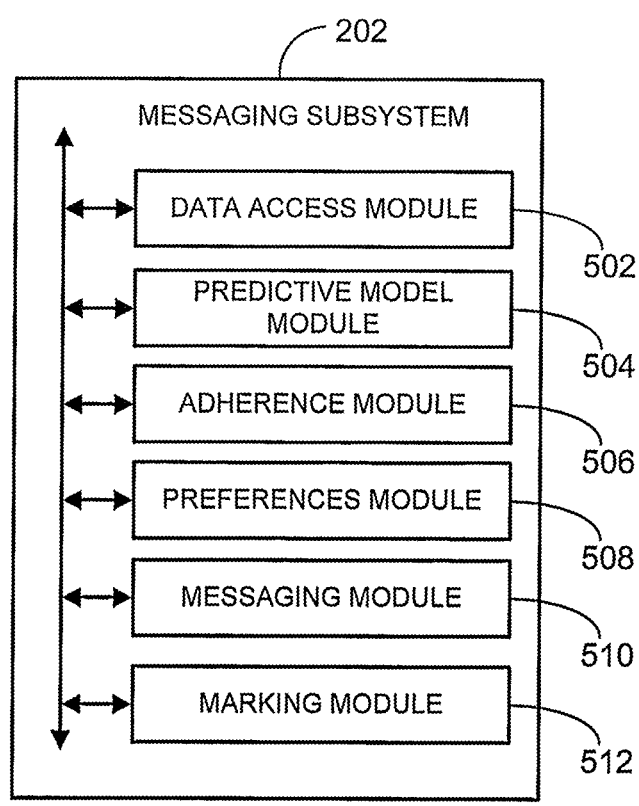
FIG. 5 is a block diagram of an example messaging subsystem that may be deployed within the benefit manager device of FIG. 2 or the pharmacy messaging device 108 of FIG. 3, according to an example embodiment.

FIG. 5 illustrates an example messaging subsystem 202 that may be deployed in the benefit manager device 106, the pharmacy messaging device 108, or otherwise deployed in another system. One or more modules are communicatively coupled and included in the messaging subsystem 202 to generate of a message to a member. The modules of the messaging subsystem 202 that may be included are a data access module 502, a predictive model module 504, an adherence module 506, a preferences module 508, a messaging module 510, and a marking module 512. Other modules may also be included.

In some embodiments, the modules of the messaging subsystem 202 may be distributed so that some of the modules are deployed in the benefit manager device 106 and some modules are deployed in the pharmacy messaging device 108. In one embodiment, the modules are deployed in memory and executed by a processor coupled to the memory. The functionality contained within the modules 502-512 may be combined into a lesser number of modules, further divided among a greater number of modules, or redistributed among existing modules. Other configurations including the functionality of the modules 502-512 may be used.

In some embodiments, the data access module 502 receives uploaded images from a member for inclusion in messages in future filled prescriptions. Images may be motivational or to stimulate memory. For example, an image of a member's loved ones may be uploaded to provide motivation for adherence to a prescription drug therapy regimen. Other images may remind a member to refill or renew a prescription. Still, yet other images may be for simple aesthetics to enliven an otherwise dull prescription container. Aesthetic images may include symbols or logos, such as those of sports teams and universities. Images may be requested by the client instead of or in addition to the member. That is, the client may provide company logos, custom identification parameters and/or custom reminders, such as "Take your meds", "Stay healthy", or the like. Images may be stored in the database 112 as at least part of the member data 114 and/or the client data 116. In addition, the data access module 502 may receive and utilize scrolling images, text, video, 3D projections, or text images.

In some embodiments, the data access module 502 administers one, or more than one, question regarding demographics to the member (e.g., via the patient device 102). Answers may be recorded in the database 112 as at least part of the sampling data 124. The data access module 502 may provides resources to members to educate them on topics, such as generic pharmaceuticals, special programs (e.g. automatic refills), diseases and health tips. The topics may be customized based on other available data.

The predictive model module 504 may utilize the member data 114, the client data 116, the claims data 118, the clinical data 120, the adherence data 122, and/or the sampling data 124 accessed by the data access module 502 to create and/or use a predictive model that predicts a meaningful message to transmit to the member based on a set of rules and/or a logic process. In some embodiments, the message predicted by the predictive model module 504 is to encourage or remind the member to refill or renew a prescription. The predictive model module 504 may select from a list of messages or may select portions of different messages and combine them together into a single message. The predictive model module 504 may also predict that more than one message will encourage or remind the member to refill or renew a prescription. In addition to or instead of the predictive model, the predictive model module 504 may utilize rules based prediction systems, adaptive systems such as Monte Carlo, fuzzy logic, and neural networks, or the like.

The predictive model module 504 utilizes one, or more than one, models and/or classifiers for use in predicting a meaningful message for providing to the member. That is, the predictive model module 504 may predict a probability of a member complying with his/her prescription drug therapy regimen by refilling or renewing the prescription before the scheduled last dose as a result of a message. The predictive model module 504 may determine the message for sending to the member that is likely to encourage prescription drug therapy adherence. The predictive model module 504 may include models and/or classifiers such as group method of data handling, naive bayes, k-nearest neighbor algorithm, majority classifier, support vector machine, logistic regression, uplift modeling, or the like.

The adherence module 506 may analyze the frequency of prescription drug claims to ascertain information on a member's prescription drug therapy regimen. In some embodiments, the adherence module 506 may analyze medical insurance claims to predict prescription drug therapy regimens needed in the future. Claims data analysis performed by the adherence module 506 may identify spot medical insurance claims that are a result of failure to comply with a prescribed drug therapy regimen.

In some embodiments, the adherence module 506 administers one, or more than one, questions regarding adherence to a prescription drug therapy regimen to the member or caregiver (e.g., via the patient device 102). Answers may be recorded in the database 112 as adherence data 122. In some embodiments, at least some of the functionality of the adherence module 506 may be deployed within a subsystem on the patient device 102.

In some embodiments, the preferences module 508 enables a member or caregiver to identify or select personal messaging preferences. For example, the preferences module 508 may generate a menu of preferences from which a member can select. In some embodiments, the preferences include preferences regarding messaging. Preferences can include a relative message priority, text, language of text, image selection, or the like. Preferences that are identified or selected with the preferences module 508 may be referenced by the messaging module 510 when generating the message to encourage refilling or renewing a prescription. Member preferences can be stored in the database 112 as at least part of the member data 114. Caregivers, such as pharmacists or their assistants, can update member preferences if, for example, the member mentions during a phone call that the automatic refill option is unwanted. In some embodiments, at least some of the functionality of the preferences module 508 and/or other modules may be deployed within a subsystem on the patient device 102.

In some embodiments, the preferences module 508 provides selection capability to the member for preferences regarding the member's filled prescription (e.g., via the patient device 102). Examples of preferences include: child proof cap or regular caps; personalized or customized messages; pertinent educational information; reminder messaging; cost savings opportunities; containers and/or lids of a desired color; images for marking an exterior of the filled prescription; size and font of text in a label or message with the filled prescription; level of adherence marked on exterior of the filled prescription; and accessories such as rings on exterior of the filled prescription.

In some embodiments, the preferences module 508 provides the member with auto refill selection and stores the member's preferences as at least part of the member data 114. Thus, the member can opt into an auto refill service for automatic prescription refills rather than making individual refill requests. The automatic refill also avoids depletion of the prescription drug as the refill prescription can be filled before the member is scheduled to take the last dose. The preferences module 508 may also provide the member with the capability of declining an auto refill service.

In some embodiments, the preferences module 508 provides the member with auto renewal selection and stores the member's preferences as at least part of the member data 114. Thus, the member can opt into an auto renewal service in which the pharmacy contacts the prescriber to renew the prescription rather than the member requesting a renewal from a prescriber. The automatic renewal avoids depletion of the prescription drug as the renewal prescription can be filled before the member is scheduled to take the last dose. The preferences module 508 also provides the member with the capability of declining an auto renewal service.

The messaging module 510 generates a message. In some embodiments, messaging module 510 stores numerous types of messages (e.g., in the database 112) and selects from stored messages to generate messages for delivery to the member.

In some embodiments, the messaging module 510 evaluates messages (or a subset of messages) according to a rules based process. The messaging module 510 references these rules for determining the appropriate message based on the message predicted by the predictive model module 504 and the member's preferences as identified by the preferences module 508. For example, the member's preference for an image to be included with the filled prescription may have a higher priority than the message generated by the predictive model module 504. A pharmacy preference may also be referenced by the preferences module 508 and be given a higher priority than the message generated by the predictive model module 504. For example, the messaging module 510 may generate a message about an available generic drug in place of the message predicted by the predictive model module 504. In contrast, a message from the predictive model module 504 may take precedence over the member's preference. For example, if the filled prescription is the last refill available and a renewal prescription is needed, a reminder message may have first priority and therefore be generated by the messaging module 510.

The messaging module 510 may store coded messages in a look-up table (e.g., in the database 112), for example. The messaging module 510 may combine messages by calling for more than one code. The coded messages may also have an address parameter associated with it so that the message may be sent to the right place for application to the filled prescription. In some embodiments, the messages are not necessarily limited to text. For example, messages may be various colored caps, colored rings on the caps, images, symbols or logos provided on the cap, scores or grades provided on the cap, or the like. When the messaging module 510 determines that the message should be a colored cap, for example, the messaging module 510 sends a signal via the network 104 to a location designated by the address parameter associated with the coded message. The location may be a pharmacy (e.g., the pharmacy fulfillment device 110), a cap manufacturer or inventory department, for example.

In some embodiment, the marking module 512 directs the marking subsystem 302 to mark on a message on a prescription cap. The message may be the messaged generated by the messaging module 510. In some embodiments, the marking module 512 directs other items to be marked.

An example implementation of the messaging subsystem 202 is as follows. The data access module 502 accesses data from the database 112 or from other sources such as PBMs, hospitals, or government agencies. The data access module 502 provides the accessed data to the predictive model module 504 that, in some embodiments, represents the member's total state for analysis.

The data access module 502 may access the claims data 118 (e.g., medical insurance claims that are a result of failure to comply with a prescribed drug therapy regimen), the clinical data 120, the adherence data 122, and the sampling data 124 associated with the member.

Based on the gathered adherence data 122, the adherence module 506 may calculate a score representing a level of adherence to the prescribed drug therapy regimen by the member. In some embodiments, the adherence module 506 rates the member's level of adherence with a grade. For example, if the member followed the prescription drug therapy regimen perfectly, the adherence module 506 may generate a grade of A. However, if the member missed a few doses, the adherence module 506 may generate a grade of B+. In other embodiments, the adherence module 506 may provide the data in other formats as utilized by the messaging subsystem 202. The level of adherence as a score or a grade may be included in the message to the member and is not necessarily solely used as an input.

Using the accessed data, the predictive model module 504 may predict a message that causes a favorable response. For example, refill messages may be selected by the predictive model module 504 based on a member's low adherence score. An example of a logic process that, in some embodiments, occurs in the predictive model module 504 is shown in Table 1.

TABLE 1

| 1. Is automatic refill option selected? | Y | See Step 2 |
| | N | Provide automatic refill message |
| 2. Is level of adherence below a desired threshold? | Y | Provide message regarding level of adherence |
| | N | See Step 3 |
| 3. Is filled prescription a brand name and generic is available? | Y | Provide message regarding availability of generic |
| | N | Provide message according to member's preferences |

Figure 6:
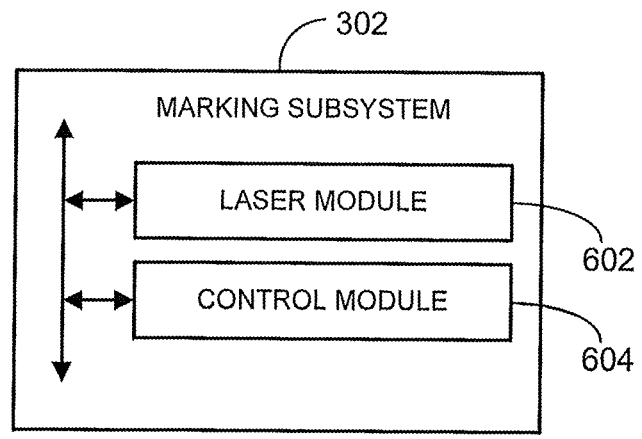
FIG. 6 is a block diagram of an example marking subsystem that may be deployed within the pharmacy messaging device of FIG. 3 or the pharmacy fulfillment device of FIG. 4, according to an example embodiment.

FIG. 6 illustrates an example marking subsystem 302 that may be deployed in the pharmacy messaging device 108, the pharmacy fulfillment device 110, or otherwise deployed in another system. One or more modules are communicatively coupled and included in the marking subsystem 302 to mark a message. The modules of the messaging subsystem 202 that may be included are a laser module 602 and a control module 604. Other modules may also be included.

In some embodiments, the modules of the marking subsystem 302 may be distributed so that some of the modules are deployed in the pharmacy messaging device 108 and/or the pharmacy device and some modules are deployed in the pharmacy fulfillment device 110. In one embodiment, the modules are deployed in memory and executed by a processor coupled to the memory. The functionality contained within the modules 602, 604 may be combined into a lesser number of modules, further divided among a greater number of modules, or redistributed among existing modules. Other configurations including the functionality of the modules 602, 604 may be used.

The laser module 602 and the control module 604 are communicatively coupled and included in the marking subsystem 302 to enable marking of prescription containers' caps with graphics, such as text or images. The laser module 602, in some embodiments, may be configured to mark multiple caps at the same or substantially the same time. The control module 604 controls and instructs the laser module 602 for marking some or all of the caps. In some embodiments, the caps are on prescription containers aligned in a specified configuration on a pallet.

Figure 7:
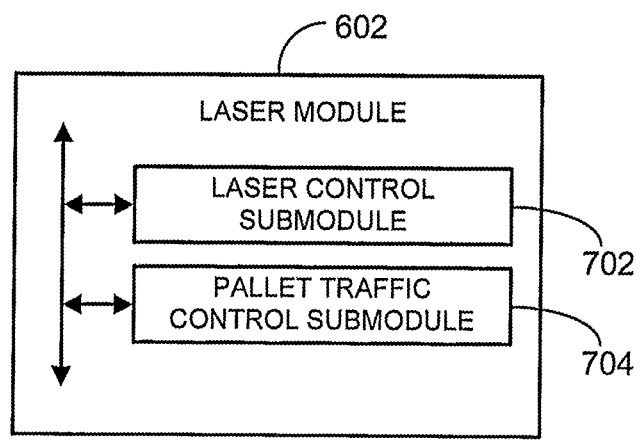
FIGS. 7 and 8 are block diagrams of example laser modules that may be deployed in the marking subsystem of FIG. 6, according to example embodiments.

In some embodiments, functionality of the control module 604 may be separated into a laser control submodule 702 and a pallet traffic control submodule 704 as shown in FIG. 7.

Figure 8:
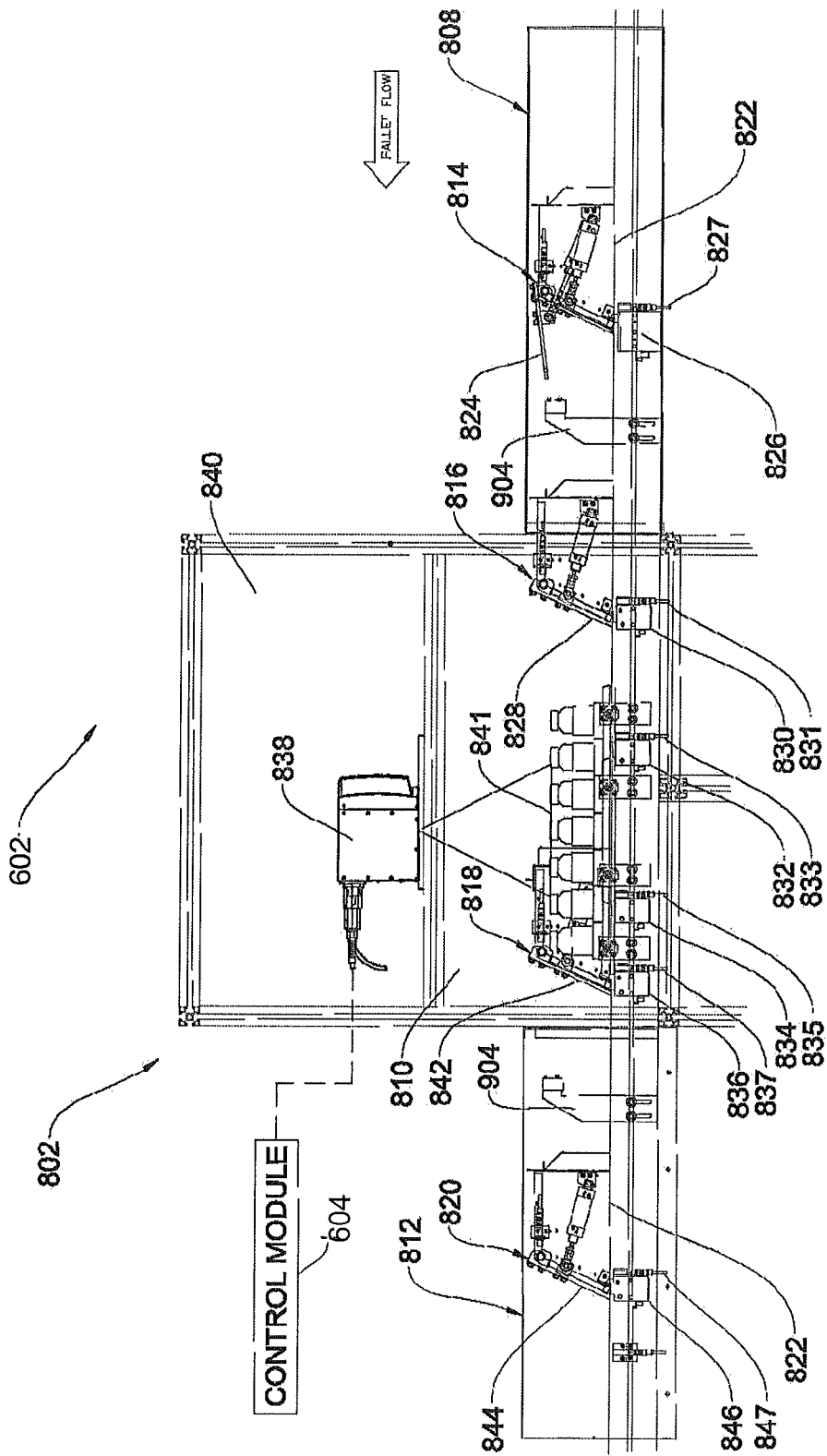

FIG. 8 illustrates an example marking subsystem 302 that may be deployed in the pharmacy messaging device 108, the pharmacy fulfillment device 110, or otherwise deployed in another system. The embodiment shown in FIG. 8 shows the modules 602, 604 described in FIG. 6 above in communication with certain hardware components.

As shown, the laser module 602 has an entry tunnel 808, a marking chamber 810 and an exit tunnel 812. The entry tunnel 808 and the exit tunnel 812 are disposed adjacent the marking chamber 810 on different sides of the marking chamber 810. The entry tunnel 808 directs the pallet 806 to the marking chamber 810. The exit tunnel 812 directs the pallet 806 away from the marking chamber 810. First and second entry gate sections 814, 816 are sequentially disposed in the entry tunnel 808. First and second exit gate sections 818, 820 are sequentially disposed in the exit tunnel 812. First and second entry gate sections 814, 816 and first and second exit gate sections 818, 820 block a path of light from the marking chamber 810.

The pallet 806 passes through a series of stop points as it navigates through the laser module 602 on a transporter 822 (e.g., a conveyor). Specifically, the first entry gate section 814 includes a first entry gate 824 and a first entry gate stop 826. The first entry gate 824 is pivotally disposed so as to open for entry of the pallet 806 or close to block light and/or contaminants. The first entry gate stop 826 is configured and arranged to stop the pallet 806 before passing through the first entry gate 824 on the transporter 822. The first entry gate stop 826 may be located at a bottom portion of the first entry gate section 814 near the transporter 822 to catch the pallet 806 and hold it stationary relative the moving transporter 822. The second entry gate section 816 includes a second entry gate 828 and a second entry gate stop 830. The second entry gate 828 is pivotally disposed so as to open for entry of the pallet 806 or close to block light and/or contaminants. The second entry gate stop 830 is configured and arranged to stop the pallet 806 before passing through the second entry gate 828 into the marking chamber 810 on the transporter 822. The second entry gate stop 830 may be located at a bottom portion of the second entry gate section 816 near the transporter 822 to catch the pallet 806 and hold it stationary relative the moving transporter 822. The first and second entry gate stops 826, 830 may be configured to allow passage of the pallet 806 when the respective entry gate 824, 828 is open for entry of the pallet 806.

The marking chamber 810 may include a laser pre-stop 832, a first laser stop 834, a second laser stop 836, one or multiple laser heads 838 and a laser safety glass panel 840. The laser pre-stop 832 is a stop point that may be positioned at the transporter 822 after the second entry gate section 816. The laser pre-stop 832 may stop the pallet 806 so that it is partially in the marking chamber 810 and partially in the opened second entry gate section 816. The first laser stop 834 may be located in the marking chamber 810 under the laser head 838 or adjacent a marking area 841 of the laser head 838. The second laser stop 836 may be located adjacent the first laser stop 834 under the laser head 838 or adjacent the marking area 841 of the laser head 838. The laser safety glass panel 840 is provided on one, or more than one, sides of the marking chamber 810. The laser safety glass panel 840 may be opaque or translucent for viewing into the marking chamber 810. The marking chamber 810 may have one, or more than one, fume extractors (not shown) to remove fumes produced when the laser head 838 marks the caps.

The pallet 806, as shown in FIG. 8 is located at both the first laser stop 834 and second laser stop 836 for illustrative purposes only. The pallet 806 does not ordinarily reside in both locations at the same time.

Figure 9:
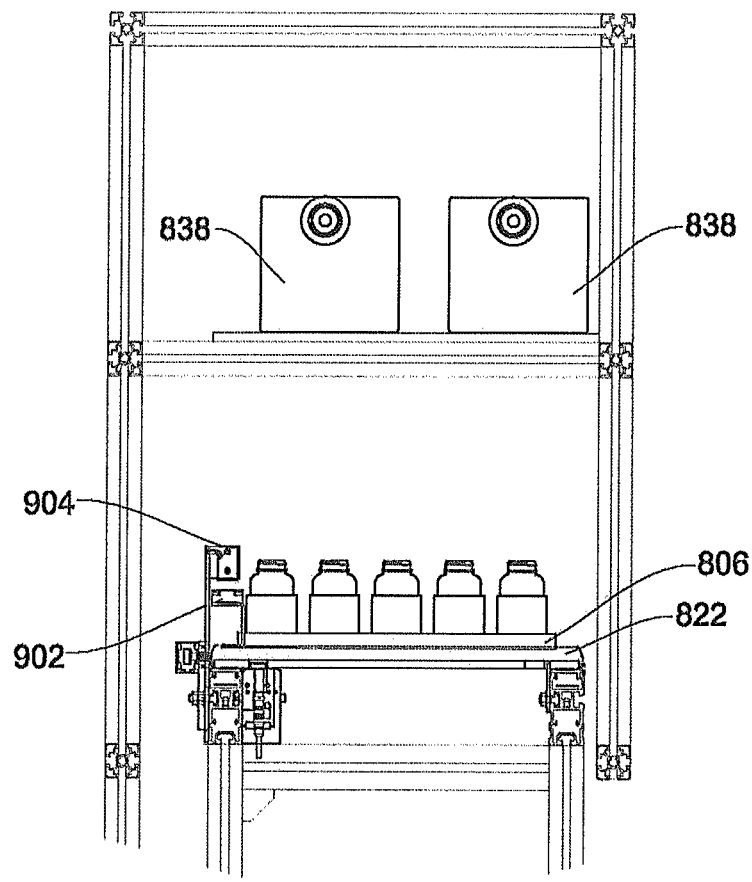
FIG. 9 is a partial cross sectional view of a laser module of FIG. 8, according to an example embodiment.
Figure 10:
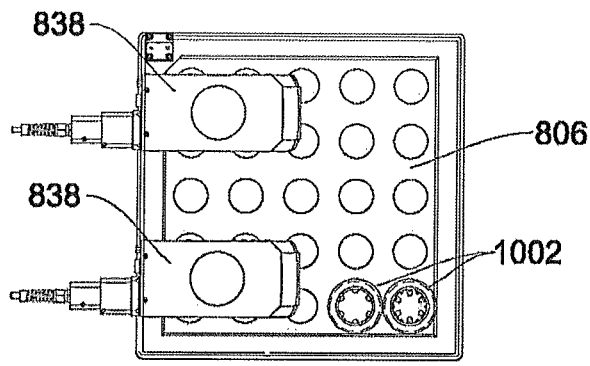
FIG. 10 is a partial top view of the laser module of FIG. 8, according to an example embodiment.
Figure 11:
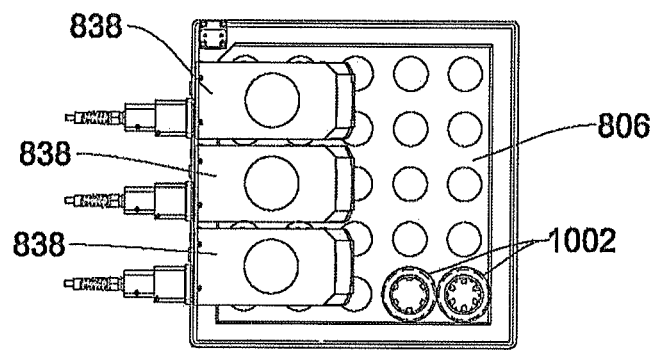
FIG. 11 is a partial top view of the laser module having three laser heads, according to an example embodiment.
Figure 12:
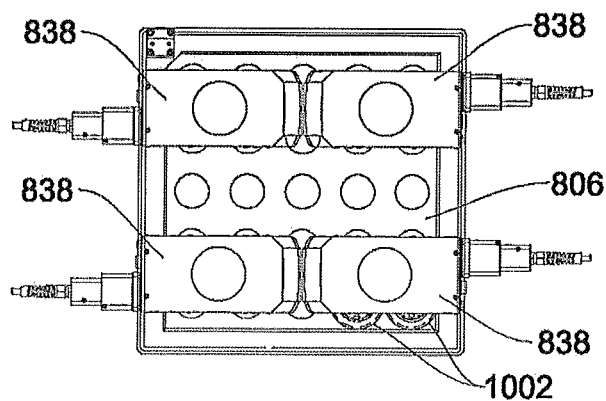
FIG. 12 is a partial top view of the laser module having four laser heads, according to an example embodiment.
Figure 13:
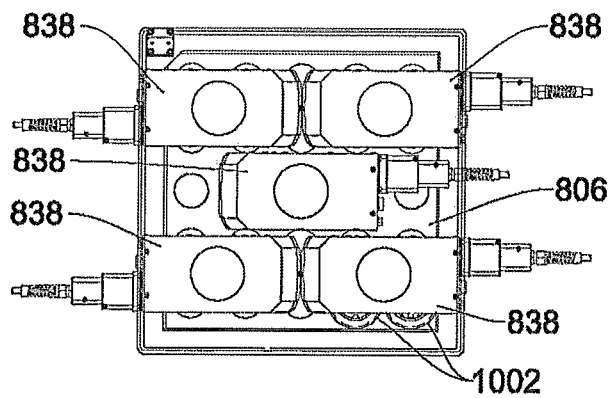
FIG. 13 is a partial top view of the laser module having five laser heads, according to an example embodiment.
Figure 14:
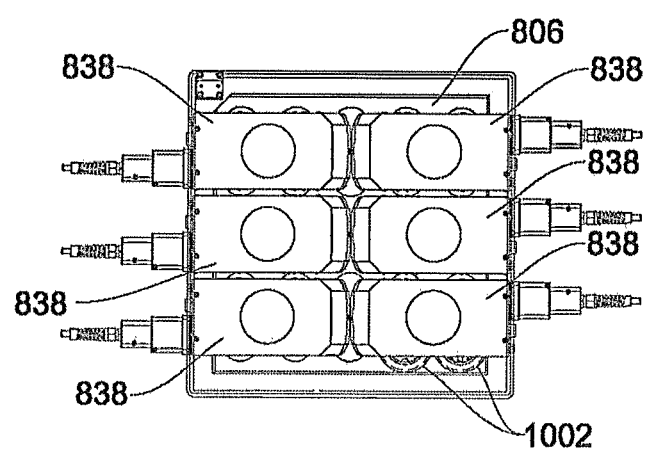
FIG. 14 is a partial top view of the laser module having six laser heads, according to an example embodiment.

Referring to FIGS. 9 and 10, within the marking chamber 810, multiple laser heads 838 are positioned above the pallet 806 with a laser reach capability sufficient to cover a width of the pallet 806 with laser beams. A single laser head 838 may be used in the event that a single laser head 838 has the laser reach capability to reach the entire upper area of the pallet 806. The pallet 806 and/or the laser head 838 may be movably disposed in the marking chamber 810 so that the laser head 838 is capable of reaching the entire upper area of the pallet 806. The laser head 838 directs laser beam travel. In an example embodiment, at least two laser heads 838 are installed, each laser head 838 covering a marking area 841 of approximately ¼ of the pallet 806 with partial overlapping of the marking areas 841. In some embodiments, the marking areas 841 do not overlap. The control module 604 chooses the optimal laser head 838 to mark the caps to optimize flow of the pallets 806 through the series of stops 834, 836 within the marking chamber 810. The laser head 838 is a wide area laser device having a marking area 841 of approximately 300 mm×300 mm, for example. In this embodiment, the laser head 838 is affixed in the marking chamber 810 above the pallet 806 having an array of containers. The laser head 838 is positioned such that its focal point is approximately focused at the height of the container's cap. This causes the laser head 838 to mark the cap with optimum clarity and avoid diffusion. Diffusion from the focal point causes the mark to become light because there is diversion from the focus and the beam expands over more surface area. Thus, the power per square inch is less. The marking area 841 may be vertically adjusted approximately ±21 mm, for example, if the laser used supports this capture. Adjusting the physical vertical position of the laser head 838 can be made, when desired, such as when the laser head 838 does not contain a vertical focal point adjustment. For the laser head 838 with vertical adjustment capability (e.g. 3D marking capability), caps at different heights may be marked. In an example, the heights of the caps may vary within approximately 42 mm of each other.

FIG. 9 illustrates a tag 902 (e.g. RFID tag) or label attached to the pallet 806 or the prescription container is read by an RF interface 904 at the second entry stop 830. FIG. 10 illustrates adapter inserts 1002 for the pallet 806. The adapter inserts 1002 has an outer diameter that allows insertion and positioning into the pallet substantially the same as the container. The adapter insert 1002 has a smaller inner diameter to hold the smaller containers, such as a 120 cc bottle. The adapter insert 1002 further includes a raised bottom portion to raise the smaller container and thereby position the cap at the marking area 841.

The first exit gate section 818 includes a first exit gate 842 pivotally disposed at the first exit gate section 818 so as to open for exiting of the pallet 806 out of the marking chamber 810 or close to block light and/or contaminants.

The second exit gate section 820 includes a second exit gate 844 and an exit gate stop 846. The second exit gate 844 is pivotally disposed so as to open for exiting of the pallet 806 or close to block light and/or contaminants. The second exit gate stop 846 is configured and arranged to stop the pallet 806 before passing through the second exit gate 844 on the transporter 822. The second exit gate stop 846 may be located at a bottom portion of the second exit gate section 820 to catch the pallet 806 and hold it stationary relative the moving transporter 822.

The stops 826, 830, 832, 834, 836, 846 include proximity sensors 827, 831, 833, 835, 837, 847 connected to the control module 604 to detect the presence of the pallet 806. The proximity sensors 827, 831, 833, 835, 837, 847 indicate whether a pallet 806 is present at the stop 826, 830, 832, 834, 836, 846. In this way the pallet 806 locations are known by the control module 604, and pallet 806 traffic can be controlled.

The closed first entry gate 824 blocks potentially harmful light when the second entry gate 828 is open or partially open. Conversely, the closed second entry gate 828 blocks potentially harmful light when the first entry gate 824 is open or partially open.

The closed first exit gate 842 blocks potentially harmful light when the second exit gate 844 is open or partially open. Conversely, the closed second exit gate 844 blocks potentially harmful light when the first exit gate 842 is open or partially open.

Thus, marking may occur in the marking chamber 810 without waiting for the second entry gate 828 and the first exit gate 842 to close. In other words, marking may occur at any time the pallet 806 is present in the marking chamber 810 regardless of the position of the immediately adjacent second entry gate 828 and first exit gate 842. One entry gate 824, 828 and one exit gate 842, 844 are closed when the pallet 806 is in the marking chamber 810. The entry gate 824, 828 and the exit gate 842, 844 that is not closed may be controlled to be open or partially open.

In operation, the laser module 602 utilizes the first and second entry gate sections 814, 816 of the entry tunnel 808 and the first and second exit gate sections 818, 820 of the exit tunnel 812 to increase throughput of the pallets 806 through the marking chamber 810 and thus decrease pallet cycle time. This is accomplished through timing of opening and closing of the gates 824, 828, 842, 844. Timing and duplicate gates 824, 844 remove open/close time of gates 828, 842 from the cycle time of the pallets 806.

For a pallet 806 having containers for marking, the transporter 822 moves the pallet 806 to the entry tunnel 808. The pallet 806 may come to rest at the first entry gate stop 826 if, for example, marking of other caps is not complete. The transporter 822 may move the pallet 806 through the opened first entry gate section 814. The pallet 806 may come to rest at the second entry gate stop 830 adjacent the second entry gate 828. The first entry gate 824 is then closed and scanning or imaging of the pallet 806 and/or its containers may occur. As soon as the first entry gate 824 is fully closed, the second entry gate 828 is permitted to open since the first entry gate 824 protects against stray laser light exiting out of the marking chamber 810. When the proceeding pallet 806 clears the laser pre-stop 832, the pallet 806 is permitted to advance to the laser pre-stop 832, positioning the pallet 806 closer to the preceding pallet 806 in the process and reducing the travel time for the pallet 806 transitioning. When the preceding pallet 806 is finished in the marking chamber 810, it is permitted to advance past the open first exit gate 842, provided that the first exit gate 842 is open. When the marking chamber 810 has been evacuated, the pallet 806 may move into the first or second marking position, where it will come to rest at the first laser stop 834 or the second laser stop 836. When the pallet 806 is no longer in the way of the second entry gate 828, the second entry gate 828 may close. After this event, the first entry gate 824 will once again open to receive a new pallet 806 and an entry tunnel sequence of opening and closing gates 824, 828 can begin again.

The pallet 806 comes to rest at the first laser stop 834 to wait for laser marking by one of the laser heads 838 to be completed. At the first laser stop 834, the laser head 838 may mark any caps needing to be marked within the marking area 841. The laser heads 838 work together to share workload. Each laser head 838 includes a marking area 841 or grid upon which it can reach with a laser beam. If two or more marking areas 841 overlap each other, the control module 604 or laser software is capable of delegating workload to the laser heads 838. If one laser head 838 has more caps to mark in an unshared or non-overlapping portion of its marking area 841, the other laser head 838 may be capable of evening the workload by performing the task of marking the caps in the overlapping portion of the marking area 841.

Examples of other laser head 838 configurations for marking are shown in FIGS. 11-14. More or less than two laser heads 838 may be provided to expand or adjust the marking area 841, increase capacity and/or accelerate marking of caps. The additional configurations of FIGS. 11-14 can also be used for larger pallets 806 or pallets 806 with differing densities of containers (i.e. containers are spaced closer together or farther apart).

Additionally, the pallet 806 may be configured to include a single laser head 838. A pallet configuration could be narrow enough such that the width of the pallet 806 does not extend beyond the marking range, or, the pallet or laser is able to index, accommodate larger width pallets 806. In some embodiments, inclusion of a single laser head 838 could be utilized for lower volume operations where higher speed is not required.

In some embodiments, when using more or less than 2 laser heads 838, the configuration of bottles may not be palletized. For example, an indexing or continuous single bottle line may be used, or, for another example, the marking occurs before the cap is placed on the bottle.

Upon completion of marking at the first laser stop 834, the pallet 806 at the first laser stop 834 may be released by causing the first laser stop 834 to unblock the pallet 806 on the transporter 822. The pallet 806 may then move toward the second laser stop 836 and come to a stop at the second laser stop 836. Any remaining caps requiring marking will be marked by the laser head 838 when the pallet 806 is at the second laser stop 836. The pallet 806 will then be released from the second laser stop 836, provided that the first exit gate 842 is not block pallet traffic.

The pallet 806 enters the exit tunnel 812 through the first exit gate 842 and, upon clearing the first exit gate 842, comes to rest at the exit gate stop 846. The first exit gate 842 then closes. Upon confirmation that the first exit gate 842 is closed, the second exit gate 844 is permitted to open. Scanning or imaging of the pallet 806 and its containers may occur once the pallet 806 has come to rest at the second exit gate 846. At this time, analysis of the markings or verification that the markings are successful may be written to the pallet tag 902, such as an RFID tag, with the RF interface 904 to indicate that all caps have their correct markings. The pallet 806 may not be released from the exit gate stop 846 until verification is complete and the second exit gate 844 is fully open.

The gates 812-818 may have proximity sensors that indicate when the gates 812-818 are closed or open. The gates 812-818 and stops are pneumatically controlled in this embodiment; although it is possible to control them in other ways. The above sequence can be controlled through a user interface, such as a PC, tablet, laptop, PLC, etc., of the control module 604.

Figure 15:
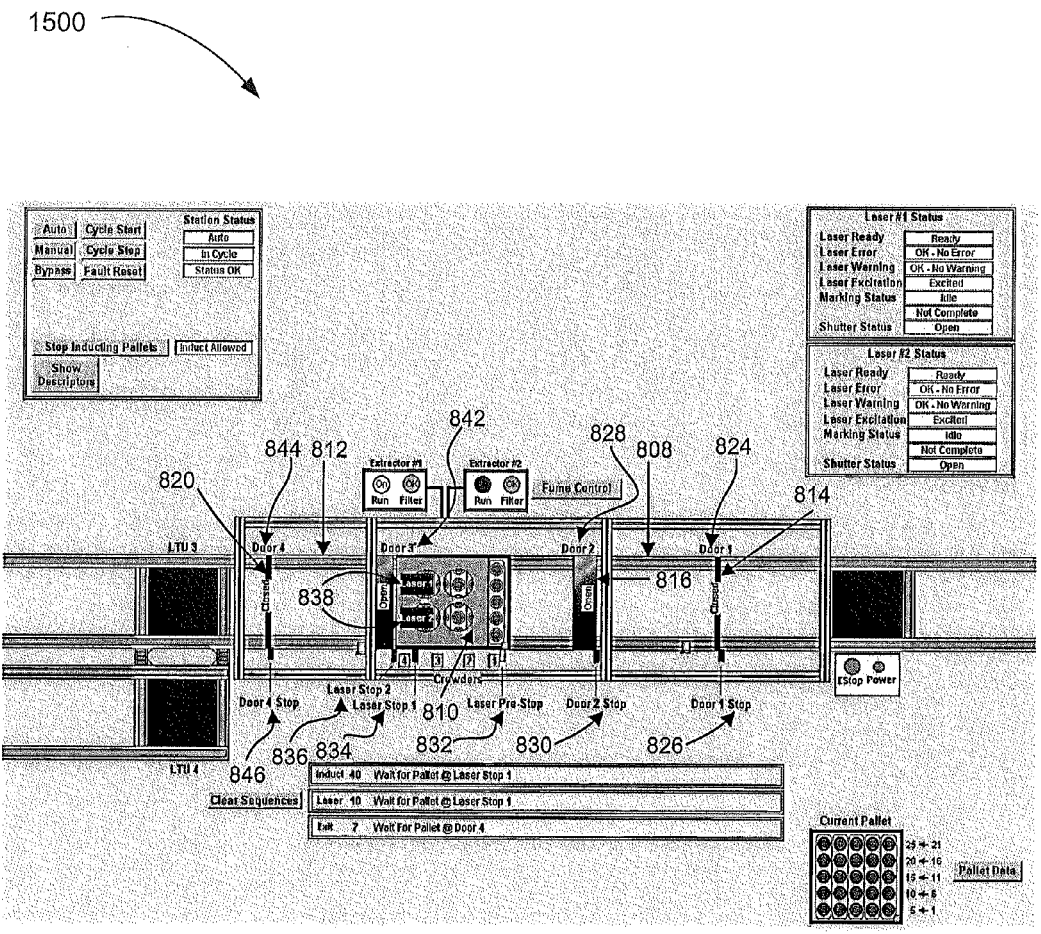
FIGS. 15 and 16 are block diagrams of example displays, according to example embodiments.

FIG. 15 shows an example of a display 1500 from the user interface. The user interface may manually control the gates 812-818 or stops 826, 830, 832, 834, 836, 846. The display 1500 may show the status of the gates 812-818 (e.g. open or closed) and the location of the pallet 806.

Once the pallet data has been read by the RF interface 904, it is sent to and received by the control module 604. The control module 604 obtains identification parameters of the prescription containers and their location. A database look up occurs (e.g. communication with the message generator device 124) to match the prescription container's ID parameters to an order and to specific order information, e.g., 0 fills remaining on the prescription matches "no refills" message. This informs the laser module 602 of the graphic subsystem 706 to mark and, since the location of each bottle is known, in which location to mark the graphics. From the prescription container ID parameter, the message generated by the message generator device 124 can be matched with its prescription container to mark the message on the container's cap.

The control module 604 controls and instructs the laser module 602 as to what to mark and determines which laser head 838 marks which cap and at which laser stop 834, 836 in the marking chamber 810. In some embodiments, the control module 604 communicates directly with the laser head 838 to instruct marking of the cap and govern timing of such marking. The control module 604 receives feedback from the laser head 838 upon execution of the marking. Communication with the laser module 602 allows the control module 604 to track the location of the pallet 806. That is, the laser module 602 communicates to the control module 604 so that the control module 604 can release the pallet 806 to the next stop 836, 846 when marking is complete. The control module 604 may include laser programs for marking the cap or laser programs may be stored in local memory on the laser head 838. A laser program may include a set of instructions for the laser head 838 to perform and may be stored in form of software. The laser programs stored on the laser head 838 may be configured in a way such that a laser program on the laser head 838 is indicative of a physical location in which the graphics appear in the marking area 841 indicative of a physical location of the particular cap. In this way, a separate laser program may exist for each cap location. A different laser program to write a specific unique message to each cap may be executed to mark only the required caps with the correct message.

For this embodiment, when one laser program is created the laser program is copied to the laser head 838 multiple times. One laser program is configured and uploaded to the laser head 838. Then text within the laser program center is centered at (0,0) on a coordinate system. When the laser head 838 is hovering over the marking area 841 on the surface of the cap, it has the ability to mark up to nine caps, for example, before it has to index or actually move the pallet 806. Once this laser program is uploaded to the laser head 838, it can be uploaded into software which can replicate and rearrange the center of the text within each laser program, while creating nine separate distinct laser programs per laser head 838 per laser stop 834, 836; the laser programs are saved back to the laser head 838. Accordingly, a laser program is now stored with the laser head 838 in the correct positions to mark each of the nine caps individually if a laser program is called correctly. This gives the ability to call an individual laser program to write information to a singular cap, without the need to modify the contents of the laser program on the fly. In some embodiments, because a single laser head's marking area 841 is large enough to mark up to nine container caps, for example, without movement, a singular program may be referenced to multiple cap locations. The laser program is modified and resaved automatically before each stop is written to.

This laser program is configured to automatically adjust or remove the messaging in each cap location within the laser program. In some embodiments, the laser head 838 may have software that replicates laser programs and stores them when creating a new message for marking. In this way only one program is created from scratch and it can then be distributed to each laser head 838 through the software which replicates the program. The text to the center location of the cap moves based on program number, and saves it to the laser head 838 in this new location.

Figure 16:
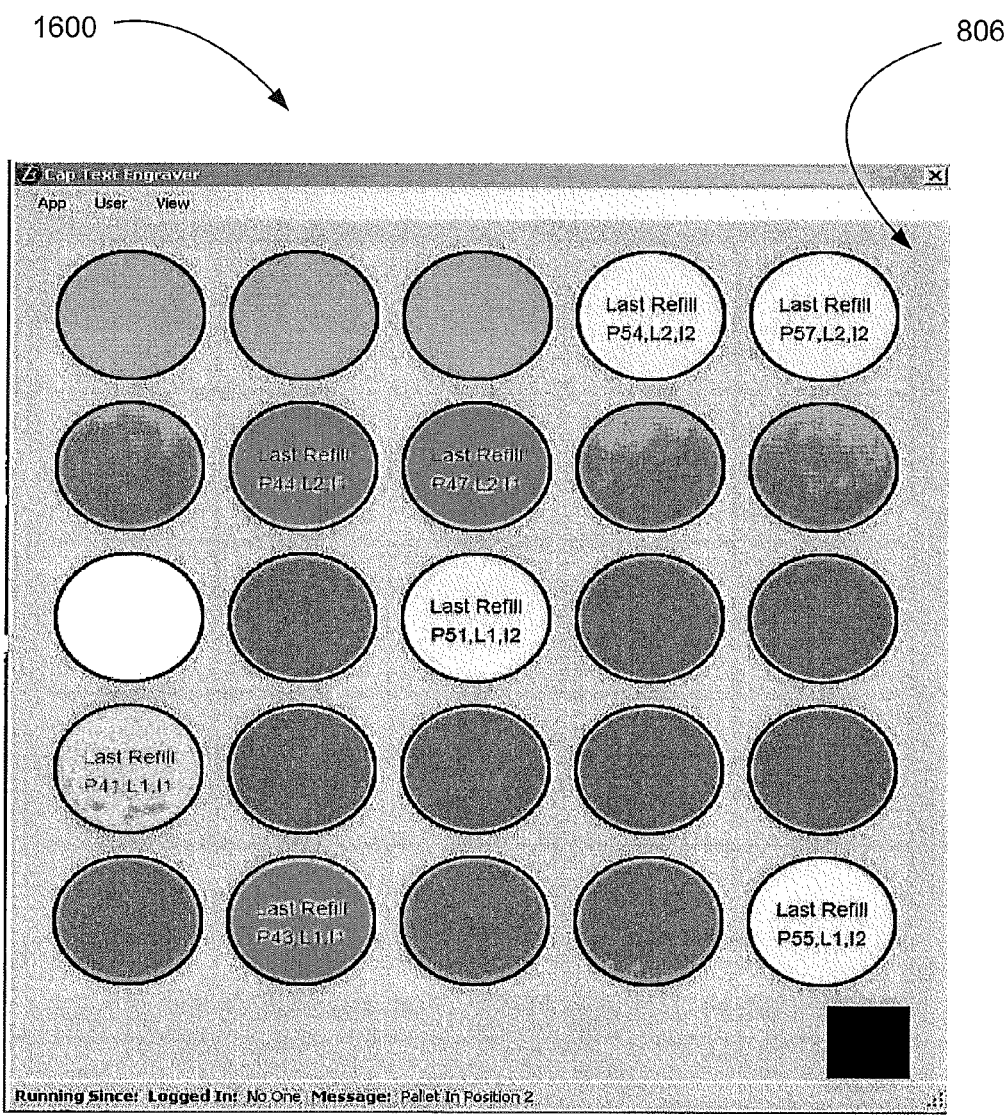

FIG. 16 is a screen shot of a display 1600 from the user interface of the control module 604. FIG. 16 illustrates control of the laser heads 838 during marking at the stops in the marking chamber 810 as the pallet 806 moves to the left. The screen shot displays the pallet 806 with the prescription containers in ordered columns and rows. It denotes caps to be marked as lightly shaded with text, caps where the mark is complete as darkly shaded with text and caps which will not be marked as darkly shaded. Additionally, when there is no cap present to be marked in a position, it may be marked white. The display 1600 may update automatically as caps are successfully marked The laser head 838 may include a fiber laser marker, such as that from Keyence America of Itasca, Ill. Generally, the laser head 838 may include a laser controller which generates laser power and houses the software and a fiber cable for laser strength buildup. The laser head 838 directs beam travel onto the cap and may turn the laser on and off in short pulses. Different types of lasers, such as a YAG laser may be implemented. The laser head 838 may produce a laser beam that is within the range of 1 to 100 Watts, for example. The power in the proper range provides a mark on the cap and does not melt the cap. The ideal power will also dictate speed because if the power is too low, more time is needed for the laser to mark the cap. Thus, power can be used to optimize speed and the visual effect of the marking on the cap.

The cap can be comprised of material such as polypropylene and one, or more than one, additives such as that from PolyOne Corporation of Avon Lake, Ohio or Ampacet Corporation of Tarrytown, N.Y. The additive causes the surface of the cap where the laser beam made contact to turn a color is distinguished from the rest of the cap. For example, additives may be used that will cause the surface to turn black when contacted with the laser beam of the laser head 838. Other additives can be used that make chromatic marks, such as red or blue.

In some embodiments, the cap is composed of material such as polypropylene with no additive. A colorant, such as a black colorant, is applied to the cap resin to cause the polypropylene to appear black. The black colorant includes properties that react with the laser beam. For example, the laser mark on the black cap may appear light gold or white.

Figure 17:
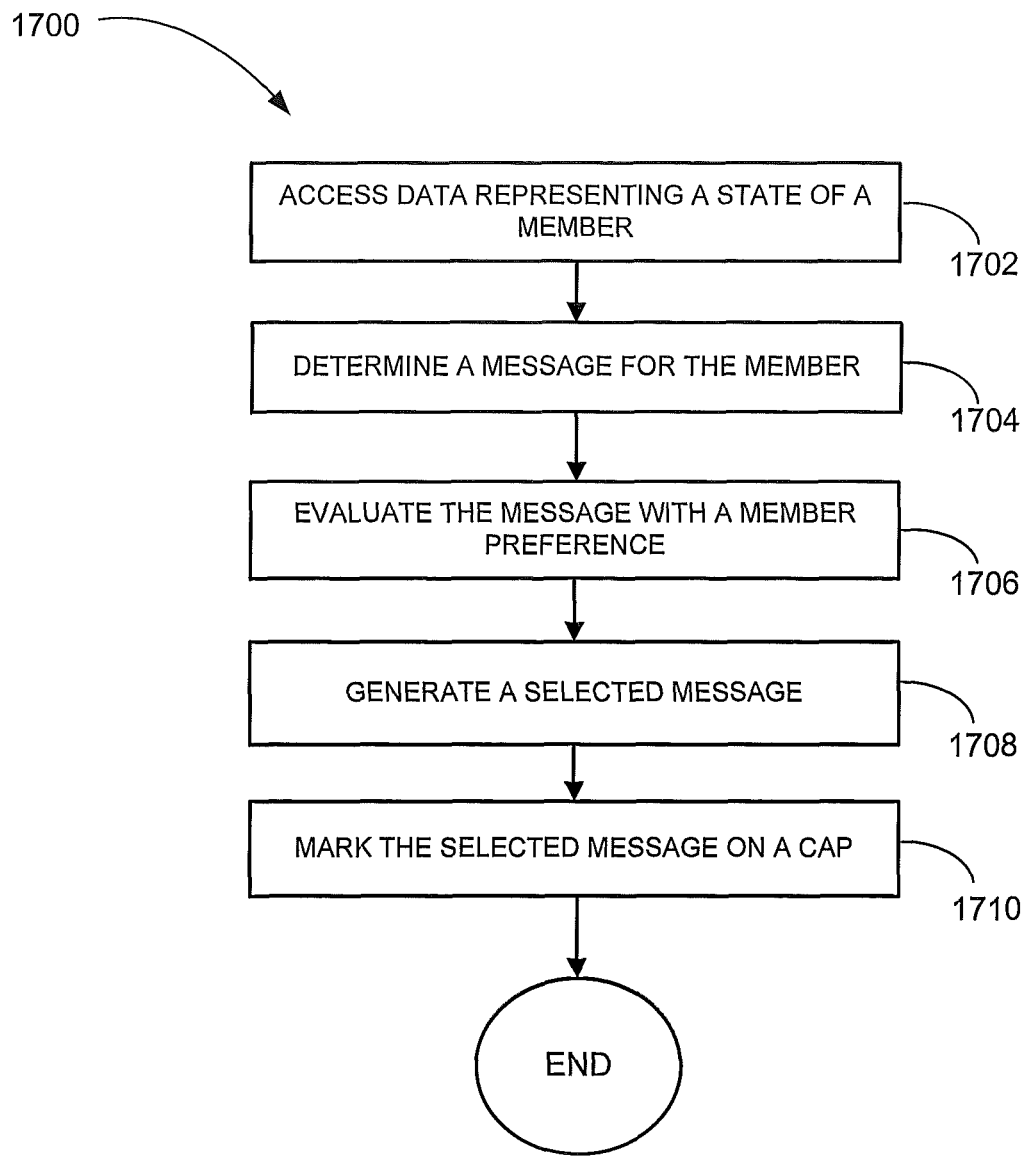
FIG. 17 is a block diagram of a flowchart illustrating a method for prescription messaging, according to an example embodiment.

FIG. 17 shows a method 1700 for pharmacy messaging, according to an example embodiment. The method 1700 may be performed partially by the patient device 102, the benefit manager device 106, the pharmacy messaging device 108, the pharmacy fulfillment device 110, partially by one, or more than one, of the foregoing devices 102, 106, 108, 110, or may be otherwise performed.

At block 1702, data representing a state of the member is accessed. The accessed data may include member data 114, client data 116, claims data 118, clinical data 120, adherence data 122 and/or sampling data 124 from the database 112. The data may be otherwise accessed.

At block 1704, a message for the member is determined. The message may be intended to or be likely to encourage prescription drug therapy adherence by the member. In some embodiments, the operations performed at block 1704 include a predictive model determine a message from among a list or table of messages.

At block 1706, the determined message is evaluated with the member and/or client preference to select a message for generation. The evaluation may be governed by a set of priority rules that determine whether the member preference and/or client preference or the determined message should be selected. The member preference may include a preference for a personally requested message or no message.

At block 1708, the selected message is generated. Examples of generating the message may include transmitting the selected message in a text message or transmitting the data to mark on the cap of the container. The desired message is then marked on a cap at block 1710.

Figure 18:
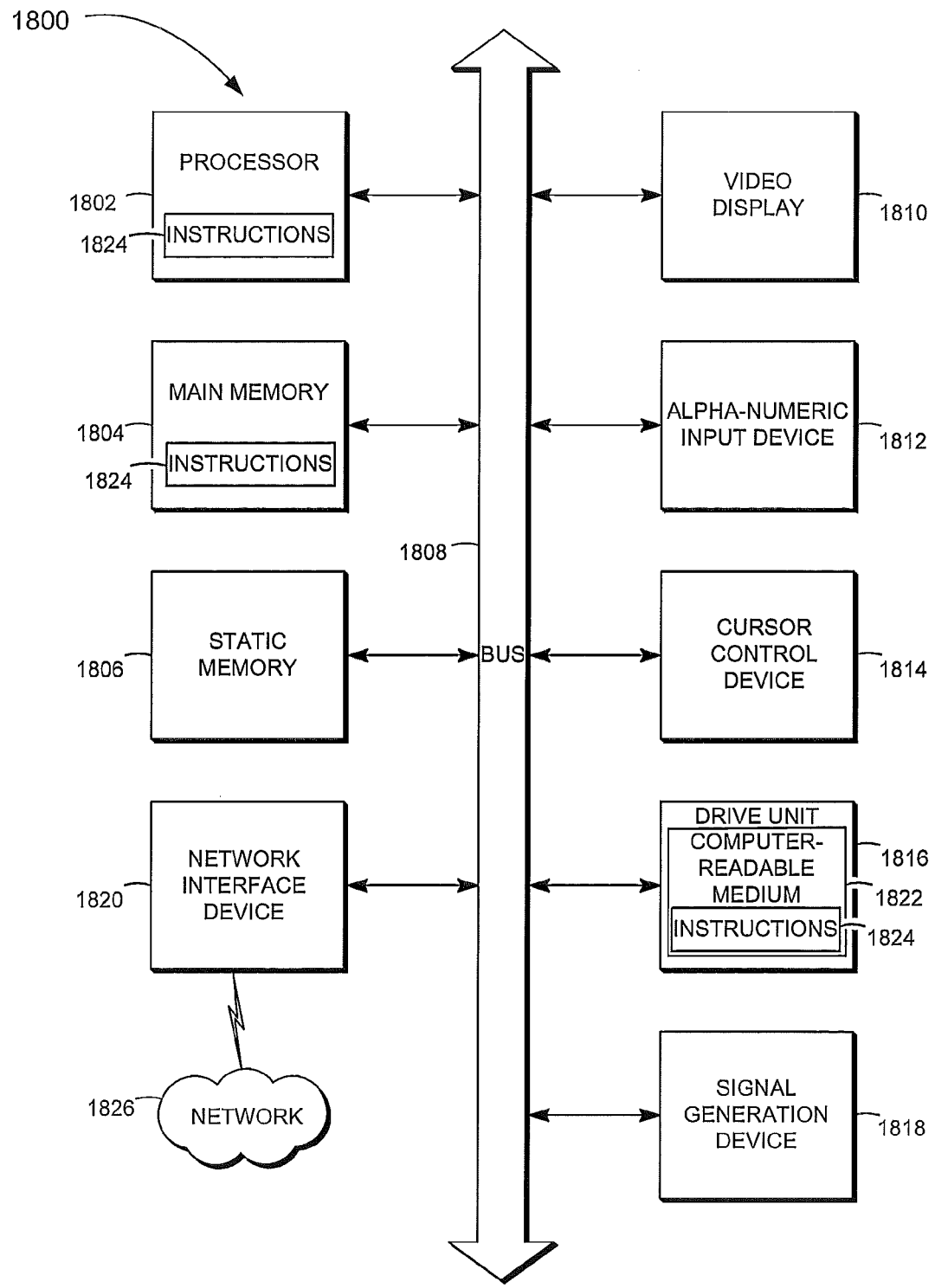
FIG. 18 is a block diagram of a machine in the example form of a computer system within which a set of instructions for causing the machine to perform any one or more of the methodologies discussed herein may be executed or stored.

FIG. 18 shows a block diagram of a machine in the example form of a computer system 1800 within which a set of instructions may be executed causing the machine to perform any one or more of the methods, processes, operations, or methodologies discussed herein. The patient device 102, the benefit manager device 106, the pharmacy messaging device 108, and/or the pharmacy fulfillment device 110 may include the functionality of the one or more computer systems 1800.

In an example embodiment, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a server computer, a client computer, a personal computer (PC), a tablet PC, a gaming device, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 1800 includes a processor 1812 (e.g., a central processing unit (CPU) a graphics processing unit (GPU) or both), a main memory 1804 and a static memory 1806, which communicate with each other via a bus 1808. The computer system 1800 further includes a video display unit 1810 (e.g., a liquid crystal display (LCD) or a cathode ray tube (CRT)). The computer system 1800 also includes an alphanumeric input device 1812 (e.g., a keyboard), a cursor control device 1814 (e.g., a mouse), a drive unit 1816, a signal generation device 1818 (e.g., a speaker) and a network interface device 1820.

The drive unit 1816 includes a computer-readable medium 1822 on which is stored one or more sets of instructions (e.g., software 1824) embodying any one or more of the methodologies or functions described herein. The software 1824 may also reside, completely or at least partially, within the main memory 1804 and/or within the processor 1812 during execution thereof by the computer system 1800, the main memory 1804 and the processor 1812 also constituting computer-readable media.

The software 1824 may further be transmitted or received over a network 1826 via the network interface device 1820.

While the computer-readable medium 1822 is shown in an example embodiment to be a single medium, the term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing or encoding a set of instructions for execution by the machine and that cause the machine to perform any one or more of the methodologies of the present invention. The term "computer-readable medium" shall accordingly be taken to include, but not be limited to, solid-state memories, and optical media, and magnetic media. In some embodiments, the computer-readable medium is a non-transitory computer-readable medium.

The term "based on" or using, as used herein, reflects an open-ended term that can reflect others elements beyond those explicitly recited.

Certain systems, apparatus, applications or processes are described herein as including a number of modules. A module may be a unit of distinct functionality that may be presented in software, hardware, or combinations thereof. When the functionality of a module is performed in any part through software, the module includes a computer-readable medium. The modules may be regarded as being communicatively coupled.

The inventive subject matter may be represented in a variety of different embodiments of which there are many possible permutations.

In an example embodiment, a system includes a laser module and a control module. The laser module includes a marking chamber with a plurality of laser heads therein. A first entry gate and a second entry gate are adjacent the marking chamber. The first entry gate is configured to open when the second entry gate is closed. A first exit gate and a second exit gate are adjacent the marking chamber at a side different from the first entry gate and the second entry gate. The first exit gate is configured to open when the second exit gate is closed. A transporter moves the objects being marked into and out of the marking chamber through the first entry gate, the second entry gate, the first exit gate, and the second exit gate. The control module is communicatively coupled to the laser module and adapted to control the laser module.

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. As used herein, "a" or "an" may reflect a single part or multiple parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies. Thus, systems and methods for pharmacy messaging have been described. Although embodiments of the present invention have been described with reference to specific example embodiments, it will be evident that various modifications and changes may be made to these embodiments without departing from the broader spirit and scope of the embodiments of the invention. Accordingly, the specification and drawings are to be regarded in an illustrative rather than a restrictive sense.

The methods described herein do not have to be executed in the order described, or in any particular order. Moreover, various activities described with respect to the methods identified herein can be executed in serial or parallel fashion. Although "End" blocks are shown in the flowcharts, the methods may be performed continuously.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

What is claimed is:

1. A system comprising:
    a laser module including
        a marking chamber with a plurality of laser heads therein,
        an entry gate adjacent the marking chamber,
        an exit gate adjacent the marking chamber at a side different from the entry gate, and
        a transporter to move objects being marked into and out of the marking chamber through the entry gate and the exit gate, the objects include a container having a cap; and
    a control module communicatively coupled to the laser module and adapted to control the laser module,
    wherein a laser head of the plurality of laser heads is directed at a marking area above a conveyor of the transporter at a height substantially the same as a height of the cap of the container disposed on the transporter, wherein each laser head of the plurality of laser heads is configured to individually mark one cap at a time;
    wherein the entry gate is in an open position to allow the objects to move into the marking chamber and a closed position to block light from the laser head;
    wherein the exit gate is in an open position to allow the objects to move out of the marking chamber and a closed position to block light from the laser head, and
    wherein the control module is to direct the laser to etch an automatic refill message if a prescription holder has not selected automatic refill, the control module is to direct the laser to etch an adherence message if automatic refill is selected and patient adherence is below a threshold, and the control module is to direct the laser to etch a generic availability message if automatic refill is selected and patient adherence is above the threshold.

2. The system of claim 1, further comprising:
    a pallet, disposed on the transporter, having the container with the cap thereon, wherein the container is a prescription drug container to hold a prescription drug.

3. The system of claim 2, wherein the marking area includes an area that a laser beam from the laser head reaches without significant diffusion so as to impede marking the cap with the laser beam.

4. The system of claim 2, wherein the marking area of the laser head does not overlap an additional marking area associated with a different laser head of the plurality of laser heads.

5. The system of claim 2, wherein the pallet includes an additional container with an additional cap thereon are in the pallet, the height of the additional cap being at a height substantially the same as the marking area.

6. The system of claim 5, wherein the control module is adapted to selectively mark the cap and to not mark the additional cap.

7. The system of claim 1, further comprising:
a message device to send a message to the control module,
wherein the cap of the container is marked with the message while the cap is located within the marking chamber.

8. The system of claim 7, wherein the message device is configured to select the message for marking from a plurality of available messages.

9. The system of claim 8, wherein selection of the message is performed by a predictive model.

10. The system of claim 8, wherein selection of the message is performed in accordance with a preference of a patient, the patient to receive prescription drug contained in the container that includes the cap.

11. The system of claim 10, further comprising:
a preference subsystem to receive a patient messaging preference,
wherein selection of the message is performed in accordance with receipt of the patient messaging preference.

12. The system of claim 10, wherein the entry gate and exit gate are linearly aligned and the transporter linearly moves objects through the linearly-aligned, entry gate and exit gates.

13. The system of claim 8, further comprising:
an image subsystem to receive an image,
wherein the message includes the image.

14. The system of claim 1, wherein the container is a prescription drug container.

15. The system of claim 1, wherein the laser head is configured to mark the cap of a filled drug container with both the entry gate and the exit gate being closed.

16. The system of claim 15, wherein the conveyor has a height less than a height of the cap and the drug container.

17. A system comprising:
a laser unit including
a marking chamber with a plurality of laser heads therein,
an entry gate adjacent the marking chamber,
an exit gate adjacent the marking chamber at a side different from the entry gate, and
a transporter to move containers being marked into and out of the marking chamber through the entry gate and the exit gate; and
a control unit communicatively coupled to the laser unit and adapted to control the laser unit, the control unit being adapted to selectively mark,
a pallet, disposed on the transporter, having a container with a cap thereon,
wherein a laser head of the plurality of laser heads is directed at a marking area above a conveyor of the transporter at a height substantially the same as a height of the cap of the container disposed within the pallet, wherein the control unit controls a first laser head of the plurality of laser heads to mark a first cap and a second laser head of the plurality of laser heads to mark a second cap; and
wherein the control module is to direct the laser to etch an automatic refill message if a prescription holder has not selected automatic refill; the control module is to direct the laser to etch an adherence message if automatic refill is selected and patient adherence is below a threshold; or the control module is to direct the laser to etch a generic availability message if automatic refill is selected and patient adherence is above the threshold.

18. The system of claim 17, wherein the entry gate is in an open position to allow the objects to move into the marking chamber and a closed position to block light from the laser head;
wherein the exit gate is in an open position to allow the objects to move out of the marking chamber and a closed position to block light from the laser head;
wherein the container is a prescription drug container to hold a prescription drug.

19. The system of claim 17, wherein the container is a prescription container,
wherein the laser head is configured to mark the cap of a filled prescription container with both the entry gate and the exit gate being closed; and
wherein the pallet has a height less than a height of the cap and the filled prescription container.

20. The system of claim 17, wherein the control module is adapted to selectively mark the cap and to not mark an additional cap;
wherein the entry gate includes a dual gate system; and
wherein the exit gate includes a dual gate system.

21. A system comprising:
a laser system including
a marking chamber with a plurality of laser heads therein,
an entry gate adjacent the marking chamber,
an exit gate adjacent the marking chamber at a side different from the entry gate, and
a transporter to move prescription drug containers with a cap to be marked into and out of the marking chamber through the entry gate and the exit gate; and
a control module communicatively coupled to the laser module and adapted to control the laser module and direct the laser module to deliver a select marking to a specific cap on a specific prescription drug container,
a pallet disposed on the transporter and having the prescription drug container with the cap thereon,
wherein a laser head of the plurality of laser heads is directed at a marking area above a conveyor of the transporter at a height substantially the same as a height of the cap of the prescription drug container disposed in the pallet on the transporter;
wherein the entry gate is in an open position to allow the pallets with a plurality of prescription drug containers to move into the marking chamber and a closed position to block light from the laser head;
wherein the exit gate is in an open position to allow the pallets with a plurality of prescription drug containers to move out of the marking chamber and a closed position to block light from the laser head;
wherein the marking area of the laser head does not overlap an additional marking area associated with a different laser head of the plurality of laser heads;
wherein the control module is to direct a first laser head of the plurality of laser heads to etch individual messages on individual ones of the caps supported in the pallet, the messages can be one of an automatic refill message if a prescription holder has not selected automatic refill, an adherence message if automatic refill is selected and patient adherence is below a threshold, a generic availability message if automatic refill is selected and patient adherence is above the threshold; and
wherein the control module is to direct a second laser head of the plurality of laser heads to etch individual messages on individual ones of the caps that are different than those being etched by the first laser head such that the system can etch two prescription drug containers simultaneously.

22. The system of claim 21, wherein the marking area includes an area that a laser beam from the laser head reaches without significant diffusion so as to impede marking the cap with the laser beam.

23. The system of claim 22, wherein the laser system includes a first laser stop in the marking chamber whereat the pallet is stopped such that a first group of prescription drug container caps is marked by the first laser head and a second laser stop in the marking chamber whereat the pallet stops such that a second group of prescription drug container caps is marked by the second laser head.

24. A system comprising:
a pallet disposed on a transporter and having a plurality of capped prescription drug containers,
a laser subsystem including
a marking chamber with a plurality of laser heads therein, a laser head of the plurality of laser heads being directed at a marking area above a conveyor of the transporter at a height substantially the same as a height of the specific cap of the specific prescription drug container disposed in the pallet on the transporter, the marking area of the laser head not overlapping an additional marking area associated with a different laser head of the plurality of laser heads,
an entry gate adjacent the marking chamber, the entry gate being in an open position to allow the pallet with the plurality of capped prescription drug containers to move into the marking chamber and a closed position to block light from the laser head,
an exit gate adjacent the marking chamber at a side different from the entry gate, the exit gate being in an open position to allow the pallet with the plurality of capped prescription drug containers to move out of the marking chamber and a closed position to block light from the laser head, and
a transporter to move the plurality of capped prescription drug containers to be marked into and out of the marking chamber through the entry gate and the exit gate; and
a control module communicatively coupled to the laser subsystem and configured to control the laser subsystem and direct the laser subsystem to deliver a select marking to a specific cap on a specific prescription drug container among the plurality of capped prescription drug containers, the control module to direct a first laser head of the plurality of laser heads to etch individual cap messages on individual ones of the plurality of prescription drug containers supported in the pallet, the messages can be one of an automatic refill message if a prescription holder has not selected automatic refill, an adherence message if automatic refill is selected and patient adherence is below a threshold, a generic availability message if automatic refill is selected and patient adherence is above the threshold, the control module to direct a second laser head of the plurality of laser heads to etch individual messages on individual ones of the plurality of prescription drug containers that are different than those being etched by the first laser head such that the laser subsystem can etch two prescription drug containers simultaneously.

* * * * *